United States Patent [19]

Ekström et al.

[11] Patent Number: 5,962,503
[45] Date of Patent: Oct. 5, 1999

[54] USE OF CHOLINESTERASE INHIBITORS IN THE TREATMENT OF XEROSTOMIA

[75] Inventors: Jörgen Ekström, Billdal; Herbert Helander, Göteborg, both of Sweden

[73] Assignee: Astra Aktiebolag, Sodertalje, Sweden

[21] Appl. No.: 08/750,825

[22] PCT Filed: Nov. 25, 1996

[86] PCT No.: PCT/SE96/01531

§ 371 Date: Dec. 13, 1996

§ 102(e) Date: Dec. 13, 1996

[87] PCT Pub. No.: WO97/19685

PCT Pub. Date: Jun. 5, 1997

[30] Foreign Application Priority Data

Nov. 29, 1995 [SE] Sweden ................................ 9504267

[51] Int. Cl.⁶ .................................................... A61K 31/40
[52] U.S. Cl. ........................................................ 514/421
[58] Field of Search .............................................. 514/421

[56] References Cited

U.S. PATENT DOCUMENTS 5,187,165   2/1993   Hamer et al. .

5,387,614   2/1995   Schoenwald et al. .

FOREIGN PATENT DOCUMENTS 9312085   6/1993   WIPO .

OTHER PUBLICATIONS

Martindale, The Extra Pharmacopoeia, 28th ed., pp. 1035–1046, 1982.

Mandel, et al., J. Oral Therapeut. Pharmacol. 4: 192–199 (1968).

Navazesh, et al., Am. J. Otolaryngol. 4:283–292 (1983).

Yu, et al., Archs. Oral Biol. 35: 209–218 (1990).

Ferguson, et al., Oral Surg. Oral Med. Oral Pathol. 75: 186–191 (1993).

*Primary Examiner*—Raymond Henley, III
*Attorney, Agent, or Firm*—White & Case L.L.P.

[57] ABSTRACT

There is provided the use of a cholinesterase inhibitor in the manufacture of a medicament for topical administration for use in the treatment of xerostomia

2 Claims, 1 Drawing Sheet

Secretion from Buccal Salivary Glands after Buccal Application of Physostigmine (1mg/ml; n=5)

USE OF CHOLINESTERASE INHIBITORS IN THE TREATMENT OF XEROSTOMIA

This is a 371 of PCT/SE96/01531 filed Nov. 25, 1996.

FIELD OF THE INVENTION

This invention relates to new use of a known class of compounds, namely choline esterase inhibitors, for topical administration to the oral mucosa in the treatment of xerostomia, as well as a method of treatment of xerostomia.

BACKGROUND OF THE INVENTION

Xerostomia, or dryness of the mouth, is a commonly experienced complaint which is characterised by diminished or arrested salivary secretion.

Saliva is secreted from numerous salivary glands, principally from the parotid, the submandibular and the sublingual salivary glands, as well as numerous minute accessory salivary glands situated just beneath the oral mucosa.

The principal functions of saliva are to keep the mucous membrane of the mouth moist, lubricate food during mastication, protect the teeth and aid the preliminary digestion of starch.

The immediate consequences of the xerostomia thus include difficulties in chewing, swallowing, speaking and interruptions of sleep patterns. More seriously, however, xerostomia has been known to result in ulcerations of the oral mucosa, dental problems including dental caries, increased frequencies of Candida, infections by Staphylococcus bacteria and, as a result of the latter, halitosis.

The causes of xerostomia are various and the condition may be subclassified along etiological lines.

Primary xerostomia arises as a consequence of pathological processes (e.g. atrophy or disease) resulting in hypofunction of the salivary glands. Primary xerostomia is also prevalent in patients having rheumatic disease (e.g. Sjögren's syndrome) as well as those undergoing radiotherapy for head and neck cancer.

The incidence of primary xerostomia is known to increase with age. For example in Sweden 15% of persons over 50 years of age complain about dryness of the mouth. This increases to 25% in persons above 70, and 33% of those above 80 years of age. As much as 40% of the hospitalised geriatric population of Sweden experience xerostomia.

Secondary xerostomia is a particularly common side effect experienced by patients taking certain pharmacological agents. Approximately half of all pharmacological agents are thought to cause xerostomia to some degree, although the problem is particularly prevalent in patients taking antidepressants and neuroleptics.

Currently available treatments for xerostomia are uncommon and include synthetic mucins (e.g. carmellose calcium, hypromellose and methylcellulose) and agents which act by reducing the viscosity of saliva in the patient's mouth (e.g. calcium sulphocyanide hexamethylenediamine; Mucidan®).

More recently pilocarpine hydrochloride has been made available for the systemic treatment of xerostomia resulting from radiotherapy. However, pilocarpine is known to produce adverse side effects involving the heart, blood pressure and digestion. Even in small daily doses, pilocarpine is known to produce profuse perspiration. U.S. Pat. No. 5,387,614 discloses the systemic treatment of xerostomia with sigma receptor ligands, namely N,N-disubstituted alkyl phenylamines, to patients.

Cholinesterase inhibitors (hereinafter designated CEIs) are known to be useful in the treatment of inter alia myasthenia gravis, glaucoma and intestinal paresis.

Pyridostigmine, a choline esterase inhibitor, have been used in patients with xerostomia, see e.g. Ferguson, M. M., Oral Surg. Oral Med. Oral Pathol., 1993:75, 191. Sustained release tablets were given orally to patients causing increase in salivary flow and increase in tear production, with variable reponse between individual patients.

Thus, there remains a need for a treatment for xerostomia which is effective and does not produce significant side effects.

Surprisingly, we have now found that CEIs are highly effective in the treatment of xerostomia, without producing any significant side-effects when administered directly to the oral mucosa, particularly at the sites of accessory salivary glands in order to stimulate salivary secretion and eliminate xerostomia.

DISCLOSURE OF THE INVENTION

According to the invention there is thus provided the use of a CEI in the manufacture of a medicament for topical administration to the oral mucosa for use in the treatment of xerostomia.

The term "xerostomia" will be well understood by those skilled in the art to comprise all forms of primary and secondary xerostomia, typically observed in human or animal patients, regardless of etiology. The term will therefore be understood to include any condition which manifests itself by way of a dryness of the mouth and/or diminished or arrested salivary secretion.

In particular we have found that CEIs when administered topically to the oral mucosa in patients suffering from, or susceptible, to xerostomia increase the volume of salivary secretion.

Thus, according to another aspect of the invention there is provided a method of treating xerostomia which comprises topically administering a therapeutically effective quantity of a CEI to the oral mucosa in a mammalian patient suffering from, or susceptible to, such a condition.

CEIs which may be mentioned include physostigmine, neostigmine bromide, neostigmine sulphate, pyridostigmine, (3aS-cis)-1,2,3,3a,8,8a-hexahydro-1,3a,8-trimethylpyrollo-[2,3-b]indol-5-yl-3,4-dihydro-2(1H) isoquinolinecarboxylate (see Example 54 of International Patent Application No SE92/00873) and (3aS-cis)-1,2,3,3a,8,8a-hexahydro-1,3a,8-trimethylpyrollo-[2,3-b]indol-5-ol (see U.S. Pat. No. 5,187,165) or a combination thereof.

According to the invention there is provided a method of treating xerostomia which comprises topical administration of a therapeutically effective quantity of a CEI to the oral mucosa of a mammalian patient suffering from, or susceptible to, such a condition.

We have found that application of CEIs to the oral mucosa stimulates production of saliva from the oral "accessory" salivary glands which, as persons skilled in the art will appreciate, are located just beneath the oral mucosa. Further, we have found that local topical application of CEIs to the oral mucosa results in sufficient secretion of saliva to alleviate xerostomia, without causing significant side effects, e.g. sweating.

CEIs may be formulated along with other ingredients commonly used in the topical administration of pharmaceutically-active compounds in accordance with known techniques.

Formulations suitable for topical administration include solutions, especially aqueous solutions. Active compounds may also be formulated for topical administration as sustained release tablets which may be located (e.g. by gluing) in close proximity to the respective salivary glands. Other modes of topical administration which may be mentioned include chewing gums, lozenges, mouth washes, and patches.

Preferred mode of topical administration is sustained release tablets.

Other ingredients which may be employed in a topical formulation will depend upon the CEI and the mode of topical administration which is employed.

The amount of pharmaceutically-active compound or compounds in the topical formulation will depend inter alia upon the CEI or CEIs which are included and the mode of topical administration which is employed. For example, when the mode of administration is via aqueous solution, it will typically comprise 0.01 to 100 mg/ml, preferably 0.05 to 25 mg/ml, and especially 0.1 to 10 mg/ml, of the pharmaceutically-active ingredients. Typical daily doses of CEI may be in the range from 0.1 to 100 mg, for example 0.2 to 25 mg and preferably 0.5 to 10 mg of the active ingredient.

CEIs may be formulated along with other active ingredients indicated for the treatment of xerostomia, for example synthetic mucins, viscosity reducing agents (e.g. mucidan) and pilocarpine.

The method of treatment according to the invention has the advantage that CEIs are extremely effective in alleviating the symptoms of xerostomia, without exhibiting significant side effects. The method of treatment according to the invention also has the advantage that CEIs may be applied locally to the oral mucosa on an "as need" basis.

The method of treatment according to the invention also has the advantage that CEIs may reach their target cells in the oral accessory salivary glands faster, at a higher concentration and may remain active for a longer period of time, compared with ways of administration previously used in the treatment of xerostomia.

The method of treatment according to the invention also has the advantage that CEIs, may be less toxic, or may have other useful pharmacological properties, compared with active ingredients previously used in the treatment of xerostomia.

TESTS

Test A
Secretion of Saliva from Salivary Glands in the Ferret

Ferrets (obtained from Mr Stig Held, Bjärshög, Sweden) were starved overnight and placed under general anaesthesia. All ducts from the major salivary glands were ligated or cannulated. Secretion of saliva from cannulated glands was monitored.

In order to provide a baseline, a dry, preweighed piece of filter paper was placed inside one cheek of the animal, removed after 5 minutes, and subsequently weighed. This procedure was repeated twice.

Test substances were applied in the form of an aqueous solution locally to the mucosa of the cheek over five minutes. Cheek saliva was collected on fresh preweighed filter papers which were changed every five minutes until secretion returned to preestablished baseline levels.

Heart rate and blood pressure were recorded continuously.
Test B
Secretion of Saliva from Accessory Glands in Human Volunteers In order to provide a baseline, a dry, preweighed piece of filter paper was placed inside the lower lip of healthy human volunteers. Saliva was collected over a fixed period of time.

A few drops of test substance were subsequently applied in the form of an aqueous solution inside the lower lip and a preweighed piece of filter paper was used to collect saliva from this spot over an equivalent period of time.

The amount of saliva collected in each case was compared.

Following the test procedure, the patient was asked if he or she had experienced any adverse side effects during or following application of the active substance.

The invention may be illustrated by way of the following examples:

EXAMPLE 1

Physostigmine (aqueous solutions; 0.1 to 10 mg/ml) was tested in Test A above.

The lowest dose (0.1 mg/ml) produced a maximal secretion of 13 $\mu$g over a five minute period; the highest dose (10 mg/ml) produced a maximal secretion of 90 $\mu$g.

With the lowest dose, secretion returned to baseline levels (3 $\mu$g over 5 minutes) 15 minutes after physostigmine was applied; with the highest dose, secretion returned to baseline levels after 100 minutes.

Slight decreases in blood pressure and heart rate were observed following administration of the highest doses only.

BRIEF DESCRIPTION OF THE DRAWING

Secretion of saliva from the buccal glands over time for the 1 mg/ml dose is represented graphically in FIG. 1.

EXAMPLE 2

Figure 1:
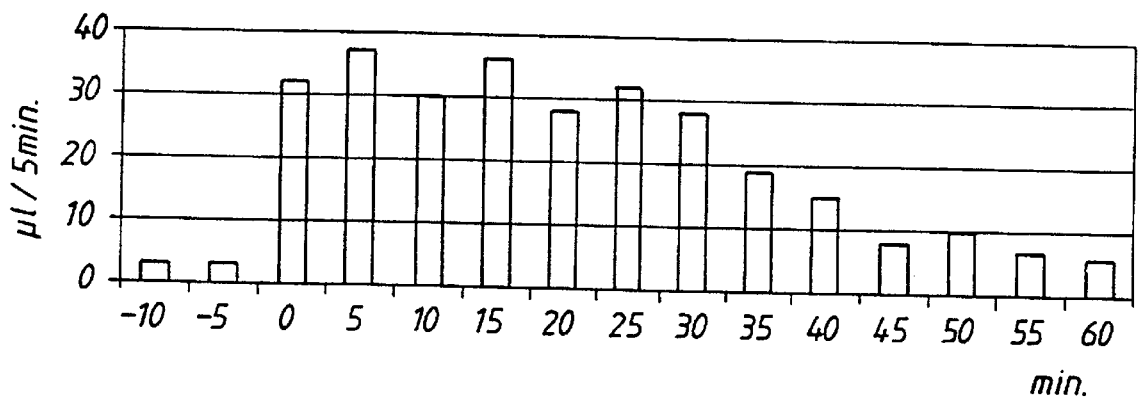

Neostigmine bromide (aqueous solutions; 0.1 to 10 mg/ml) was tested in Test A above. The highest dose (10 mg/ml) produced a maximal secretion of 60 $\mu$g over a five minute period with a secretory response duration of about 20 minutes.

EXAMPLE 3

Neostigmine sulphate (aqueous solutions; 0.1 to 10 mg/ml) was tested in Test A above. The highest dose (10 mg/ml) produced a maximal secretion of 130 $\mu$g over a five minute period with a secretory response duration of about 20 minutes.

EXAMPLE 4

Physostigmine (aqueous solution; 0.1 to 1 mg/ml) was tested in Test B above in two healthy persons. Following application, the local salivary secretion was observed to increase to about twice the baseline level, remaining increased for about 15 minutes. No side effects were observed.

We claim:

1. A method of treating xerostomia which comprises topical administration of a therapeutically effective quantity of a cholinesterase inhibitor to the oral mucosa of a mammalian patient suffering from, or susceptible to, such a condition.

2. The method as claimed in claim 1, wherein the cholinesterase inhibitor is physostigmine.

* * * * *